United States Patent
Ciampini et al.

(10) Patent No.: US 9,012,562 B2
(45) Date of Patent: Apr. 21, 2015

(54) ACRYLIC ADHESIVE FOR ASSEMBLING ELEMENTS CONTACTING BIOLOGICAL SUBSTANCES

(75) Inventors: Davide Ciampini, Arnad (IT); Lucia Giovanola, Arnad (IT); Cristina Panciatichi, Arnad (IT); Oriana Rossotto, Arnad (IT); Duccio Spartaco Sassano, Arnad (IT)

(73) Assignee: SICPA Holding SA, Prilly (CH)

( * ) Notice: Subject to any disclaimer, the term of this patent is extended or adjusted under 35 U.S.C. 154(b) by 934 days.

(21) Appl. No.: 13/142,775

(22) PCT Filed: Dec. 30, 2008

(86) PCT No.: PCT/EP2008/068370
§ 371 (c)(1),
(2), (4) Date: Jun. 29, 2011

(87) PCT Pub. No.: WO2010/075894
PCT Pub. Date: Jul. 8, 2010

(65) Prior Publication Data
US 2011/0266362 A1 Nov. 3, 2011

(51) Int. Cl.
*C08L 27/12* (2006.01)
*C08F 8/30* (2006.01)
*C09J 4/00* (2006.01)
*B01L 3/00* (2006.01)
*C09J 133/06* (2006.01)

(52) U.S. Cl.
CPC ............. *C09J 4/00* (2013.01); *B01L 3/502707* (2013.01); *B01L 2200/12* (2013.01); *B01L 2300/12* (2013.01); *B01L 2300/16* (2013.01); *C09J 133/06* (2013.01)

(58) Field of Classification Search
USPC ........... 524/544, 555, 558; 526/245, 261, 320
See application file for complete search history.

(56) References Cited

U.S. PATENT DOCUMENTS

| 4,312,916 | A | * | 1/1982 | Kakumaru et al. | ........... 428/345 |
| 4,877,745 | A | | 10/1989 | Hayes et al. | |
| 5,338,688 | A | | 8/1994 | Deeg et al. | |
| 5,899,381 | A | * | 5/1999 | Gordon et al. | ..................... 239/6 |
| 6,830,621 | B2 | | 12/2004 | Udagawa et al. | |
| 2002/0012156 | A1 | * | 1/2002 | Varaprasad et al. | .......... 359/273 |
| 2004/0242770 | A1 | * | 12/2004 | Feldstein et al. | ............. 525/54.3 |
| 2011/0183203 | A1 | * | 7/2011 | Du et al. | ....................... 429/217 |

FOREIGN PATENT DOCUMENTS

EP            1933138 A1    6/2008

OTHER PUBLICATIONS

International Search Report of PCT/EP2008/068370 dated Apr. 15, 2009.

* cited by examiner

*Primary Examiner* — Justin Jonaitis
(74) *Attorney, Agent, or Firm* — Greenblum & Bernstein, P.L.C.

(57) ABSTRACT

The present invention relates to acrylic adhesive composition comprising a mixture of at least one polyol tri(meth)acrylate monomer and at least one polyalkylene glycol mono(meth) acrylate monomer for assembling elements made of plastic materials, like PMMA or SAN, or inorganic material, like glass or metals, employed for manufacturing of devices for the distribution or containment of biological substances, like proteins, enzymes, antibodies, antigens, DNA, and the like. The present invention also relates to devices for the distribution or containment of biological substances assembled with the above mentioned acrylic adhesive composition, and particularly thermal or piezoelectric ejecting devices, and biochip microarray, as well as to a method for assembling thereof.

17 Claims, 3 Drawing Sheets

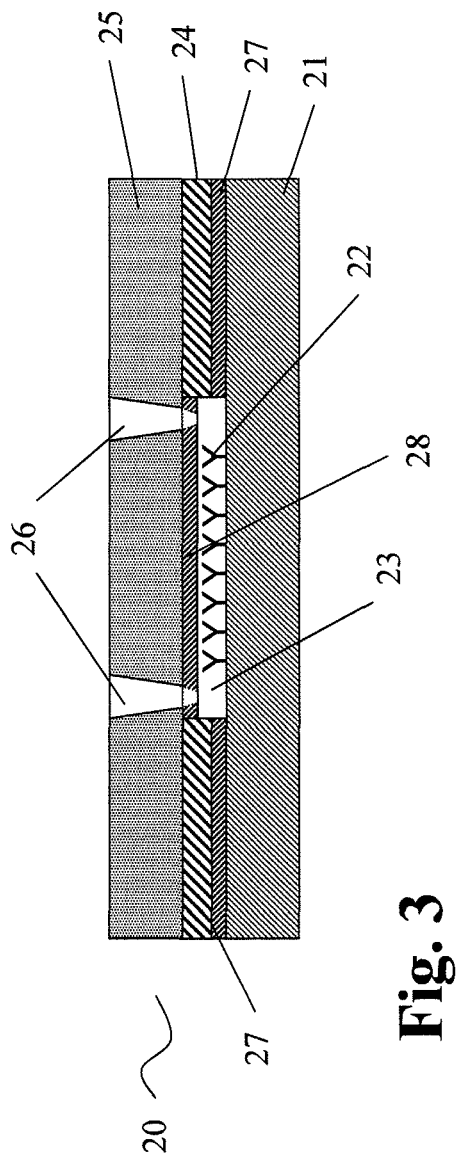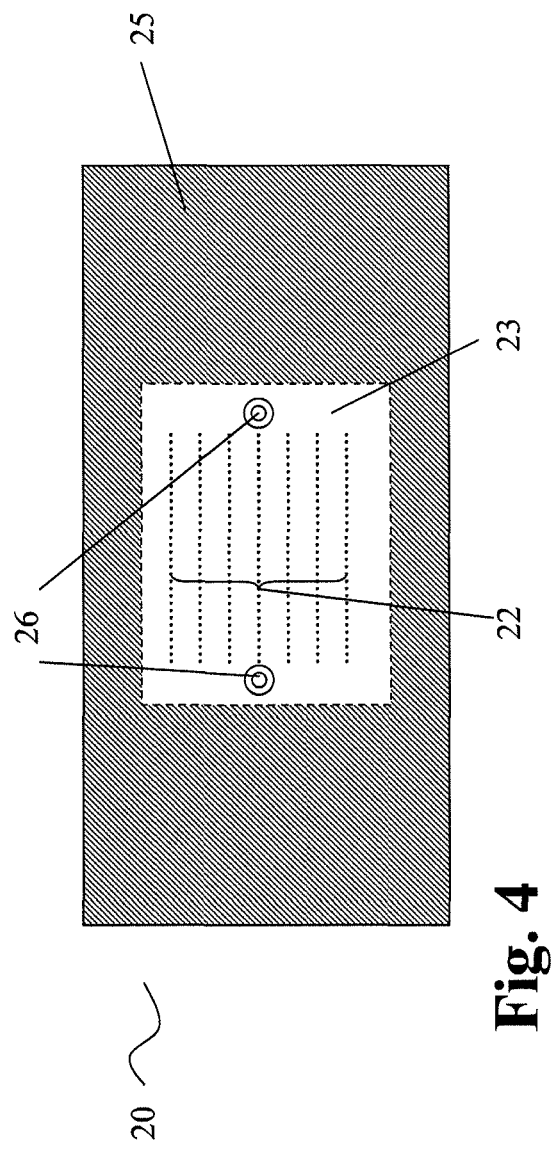

ACRYLIC ADHESIVE FOR ASSEMBLING ELEMENTS CONTACTING BIOLOGICAL SUBSTANCES

FIELD OF THE INVENTION

The present invention relates to an acrylic adhesive for assembling elements contacting biological substances and to a device assembled therewith.

More in particular, the present invention relates to acrylic adhesive composition comprising a mixture of at least one polyol tri(meth)acrylate monomer and at least one polyalkylene glycol mono(meth)acrylate monomer for assembling elements made of plastic materials, like PMMA or SAN, or inorganic material, like glass or metals, employed for manufacturing of devices for the distribution or containment of biological substances, like proteins, enzymes, antibodies, antigens, DNA, and the like.

The present invention also relates to devices for the distribution or containment of biological substances assembled with an acrylic adhesive composition, and particularly thermal or piezoelectric ejecting devices, and biochip microarray.

BACKGROUND OF THE INVENTION

In the biomedical field devices are known for the distribution or containment of biological substances, like proteins, enzymes, antibodies, antigens, DNA, and the like, dissolved in solutions or biological fluids.

Such biomedical devices are manufactured by assembling different components of different materials by adhesive compositions. Several patents and patent publications describe such kind of devices.

U.S. Pat. No. 5,338,688 describes a device for ejecting biological fluids comprising a reservoir connected with an ejection chamber provided with a heating element. U.S. Pat. No. 4,877,745 describes a similar device, wherein the ejection chamber is provided with a piezoelectric element.

U.S. Pat. No. 6,830,621 describes a liquid discharge apparatus comprising (i) a liquid holding portion for holding the probe liquid, (ii) a supply opening for supplying the probe liquid to the liquid holding portion, (iii) a liquid discharging nozzle for discharging the probe liquid, and (iv) a flow path connecting the nozzle with the liquid holding portion. The nozzle openings and the supply opening are disposed on mutually opposed faces of the apparatus. The apparatus has a laminated structure composed of a first plate-shaped member in which said nozzles are formed, and a second plate-shaped member in which said plurality of liquid supply opening are formed, and intermediate plate-shaped members in which the flow path connecting the nozzle with the liquid holding portion is realized.

EP 1,933,138 discloses microarrays of capture probes on a substrate to be used in biological assays, for instance to examine analyte biological fluids, such as human blood or tissue samples, for the presence and/or concentration of certain bacteria, viruses and/or fungi. The capture probes have a selective binding capacity for a predetermined indicative factor, such as a protein, DNA or RNA sequence. In the microarray technique, a set of specific capture probes, each of which being chosen in order to interact specifically (e.g. hybridize in the case of a DNA microarray) with one particular target biological compound, are immobilized at specific locations of a biosensor solid substrate, for instance by printing. Suitable probes may comprise bio-fluids containing the specific indicative factor, for instance a solution of a specific DNA sequence and/or antibody. After the substrate has been provided with the capture probes, for instance by printing them on the substrate using an ink jet device, the analyte fluid is forced to flow through the substrate, or is forced to flow over the substrate. In order to be able to visualize the presence of an indicative factor in the analyte fluid, molecules of the analyte fluid may for instance be provided with fluorescent and/or magnetic labeling. In case of an ELISA (enzyme-linked immunosorbent assay) an enzyme is attached to the second antibody, instead of a radiolabel. An intensely colored or fluorescent compound is then formed by the catalytic action of this enzyme. The labeled molecules of the analyte fluid adhere to those capture probes of the substrate that have binding capacity for the molecule considered. This results in a detectable fluorescence on the spot the specific factor adheres to, at least when using fluorescent labeling. The captured molecules are typically read by illumination with a light source, and the fluorescent pattern recorded with the aid of a CCD camera for instance. The recorded pattern is a characteristic of the presence of a bacterium or a set of bacteria. By providing capture probes with different specificity for different factors, the array may be used to assay for various different factors at the same time. Using such arrays enables high-throughput screening of analyte fluids for a large amount of factors in a single run.

The main problem of the biomedical devices obtained by assembling different components of different materials by adhesive compositions relates to the reduction of the adhesion strength under aging, in particular when different materials (like metals, silicon, plastics, or glass) are contacting each other and are exposed to mechanical and thermal stresses.

Moreover, the components of the biomedical devices described in the art, in particular in the microelectronic and microhydraulic fields employed in the technology derived from ink-jet printing, must be biocompatible with the biological substances. Accordingly, the component materials should not hold the biological substances on their surface and should not release any contaminant substance into the biological fluid.

Additionally, the component material surface should have a high wettability to allow an easy diffusion of the biological fluids, typically having an aqueous base, into the biomedical device. The wettability is even more important in devices containing microhydraulic conduits wherein the flow of the fluids depends on capillarity forces and interactions between the fluid and the contacting surface.

Surface treatments are known in the art to reduce the chemical and physical interactions between the material surfaces and the biological fluids, such as, for example, plasma treatment, corona treatment, or film coating. However, plasma and corona treatments have a limited duration over time. Film coating treatments which alter the material surface, can also make difficult the subsequent adhesion of the components and its strength under aging.

SUMMARY OF THE INVENTION

The Applicant has surprisingly found that the above mentioned problems can be overcome by assembling the components of a biomedical device for the distribution or containment of biological substances with an adhesive composition comprising a mixture of at least one polyol tri(meth)acrylate monomer and at least one polyalkylene glycol mono(meth)acrylate monomer.

A first aspect of the present invention relates to a biomedical device for the distribution or containment of biological substances comprising at least two components assembled each other with an adhesive composition comprising at least one polyol tri(meth)acrylate monomer and at least one polyalkylene glycol mono(meth)acrylate monomer.

In another aspect the present invention relates to a biomedical device for the distribution or containment of biological substances comprising at least one surface thereof covered with a cured acrylic composition layer having a wettability equal to or lower than 50°.

Another aspect of the present invention relates to a method for assembling a biomedical device comprising at least two components, wherein said process comprises the steps of (i) forming a film of an adhesive composition comprising at least one polyol tri(meth)acrylate monomer and at least one polyalkylene glycol mono(meth)acrylate monomer on at least one surface of said at least two components, (ii) contacting said at least one surface of said at least two components to be assembled, and (iii) curing said adhesive composition.

A further aspect of the present invention relates to an adhesive composition comprising at least one polyol tri(meth)acrylate monomer, at least one polyalkylene glycol mono (meth)acrylate monomer, and at least one radical initiator.

A still further aspect of the present invention relates to the use of the above mentioned adhesive composition for assembling the components of a biomedical device for the distribution or containment of biological substances.

The adhesive composition of the present invention comprises a mixture of at least one polyol tri(meth)acrylate monomer, at least one polyalkylene glycol mono(meth)acrylate monomer, and at least one radical initiator.

The polymerizable polyol tri(meth)acrylate monomers, used pursuant to the invention, are preferably selected from triacrylates, such as ditrimethylolpropane triacrylate (DiTMPTTA), tris-(2-hydroxyethyl)-isocyanurate triacrylate (THEICTA), dipentaerythritol triacrylate (DiPETA), ethoxylated trimethylolpropane triacrylate (TMPEOTA), propoxylated trimethylolpropane triacrylate (TMPPOTA), ethoxylated pentaerythritol triacrylate (PETEOIA), propoxylated glyceryl triacrylate (GPTA), pentaerythritol triacrylate (PETA), trimethylolpropane triacrylate (TMPTA) and modified pentaerythritol triacrylate; and trimethacrylates, such as triethyleneglycol trimethacrylate (TIEGTMA), tetraethyleneglycol trimethacrylate (TTEGTMA), polyethyleneglycol trimethacrylate (PEGTMA), trihydroxyhexane trimethacrylate (HTTMA), ethoxylated bisphenol A trimethacrylate, trimethylolpropane trimethacrylate (TMPTMA).

Preferably, ethoxylated or propoxylated polyol tri(meth) acrylate monomers are utilized in the adhesive composition. The use of ethoxylated or propoxylated polyol tri(meth)acrylate monomers improves the wettability of the resulting surfaces covered with the adhesive composition. The wettability of a cured adhesive composition layer, when measured with the contact angle method by using a drop of water contacting the adhesive composition layer, is equal to or lower than 50°, preferably lower than 40°, and more preferably lower than 35°. Also, the use of ethoxylated or propoxylated polyol tri(meth)acrylate monomers, typically having a low viscosity, allows to reduce the viscosity of the adhesive composition.

Examples of preferred ethoxylated or propoxylated polyol tri(meth)acrylate monomers include, but are not limited to, ethoxylated trimethylolpropane triacrylate (TMPEOTA), propoxylated trimethylolpropane triacrylate (TMPPOTA), ethoxylated pentaerythritol triacrylate (PETEOIA), propoxylated glyceryl triacrylate (GPTA), ethoxylated bisphenol A trimethacrylate, ethoxylated trimethylolpropane trimethacrylate (TMPETMA), commercially available, for example, from IGM Resins, under the tradename Omnimer®.

The acrylic adhesive composition of the present invention preferably comprises from about 40% to about 90% by weight, based upon the total weight of the composition, of the polyol tri(meth)acrylate monomers. According to a preferred embodiment, the adhesive composition of the present invention preferably comprises from about 50% to about 80% by weight, based upon the total weight of the composition, of the polyol tri(meth)acrylate monomers.

The polymerizable polyalkylene glycol mono(meth)acrylate monomers, used pursuant to the invention, are preferably selected from (meth)acrylates such as polypropylene glycol monomethacrylate, polyethylene glycol monomethacrylate, polyethylene glycol-polypropylene glycol monomethacrylate, polypropylene glycol monoacrylate, polyethylene glycol monoacrylate, polypropylene glycol-polytrimethylene monoacrylate, polyethylene glycol-polytetramethylene glycol monomethacrylate, methoxypolyethylene glycol monomethacrylate, perfluoroalkylethyl-polyoxyalkylene monomethacrylate, and combinations thereof. Commercial products of those compounds are available, including, for example, Blemmer PP series (polypropylene glycol monomethacrylates), Blemmer PE series (polyethylene glycol monomethacrylates), Blemmer PEP series (polyethylene glycol-polypropylene glycol monomethacrylate), Blemmer AP-400 (polypropylene glycol monoacrylate), and Blemmer AE-350 (polyethylene glycol monoacrylate). These are all products of Nippon Oils & Fats Co.

The acrylic adhesive composition of the present invention preferably comprises from about 5% to about 35% by weight, based upon the total weight of the composition, of the polyalkylene glycol mono(meth)acrylate monomers. According to a preferred embodiment, the adhesive composition of the present invention preferably comprises from about 10% to about 30% by weight, based upon the total weight of the composition, of the polyalkylene glycol mono(meth)acrylate monomers.

The Applicant has found that when the polyalkylene glycol mono(meth)acrylate monomers is added to the acrylic adhesive composition in an amount within the above mentioned range, the cured composition exhibits excellent antifouling and adhesion properties.

Moreover, the surface of the materials treated with the adhesive composition of the present invention which remain exposed, i.e., not joined to the surface of another material, resulted to be biocompatible with the biological fluids. In other words, the surface of the materials treated with the adhesive composition of the present invention neither links external components contained in the biological fluids contacting it, nor releases internal components which could alter the composition of the biological fluids contacting it.

Accordingly, the use of the acrylic adhesive composition of the present invention allows to avoid all those surface treatments, like thermal treatment, corona treatment, plasma treatment, and so on, which conventionally are employed to improve the biocompatibility and antifouling properties.

Without being limited by any theory, the Applicant believes that the biocompatibility and the antifouling properties are due to the presence on the surface of the cured composition of polyalkylene glycol chains which prevent or reduce the absorption of biomolecules like proteins, enzymes, DNA, and so on.

The free-radical polymerization of the acrylic adhesive composition of the present invention can be carried out in any manner familiar to the skilled worker, for example thermally, photochemically, and/or by means of electron beams. Preferably, the free-radical polymerization is carried out photochemically.

Accordingly, the acrylic adhesive composition of the present invention comprises from about 1% to about 25%, more preferably from about 2% to about 20% by weight based upon the total weight of the composition, of a thermal initiator (thermoinitiator) or an initiator sensitive to UV and/or blue radiation (photoinitiator). As used herein, "photoinitiator" means a suitable compound which is capable of converting the UV and/or blue radiation energy into free radicals. As used herein, "thermoinitiator" means a suitable compound which is capable of converting the thermal energy into free radicals. The presence of the free radicals initiates a chain reaction which converts reactive monomer compounds into oligomers and ultimately into polymers.

Examples of suitable photoinitiators include but are not limited to: 2,2'-(2,5-thiophenediyl)bis(5-tert-butylbenzoxazole); 1-hydroxycyclohexyl phenyl ketone; 2,2-dimethoxy-2-phenylacetophenone; xanthone; fluorenone; anthraquinone; 3-methylacetophenone; 4-chlorobenzophenone; 4,4'-dimethoxybenzophenone; 4,4'-diaminobenzophenone; Michler's ketone; benzophenone; benzoin propyl ether; benzoin ethyl ether; benzyl dimethyl ketal, 1-(4-isopropylphenyl)-2hydroxy-2-methylpropane-1-one; 2-hydroxy-2-methyl-1phenylpropane-1 one; methylbenzoyl formate thioxanthone; diethylthioxanthone; 2-isopropylthioxanthone; 2-chlorothioxanthone; 2-methyl-1-(4-(methylthio)phenyl)-2-morpholinopropane-1-one; and 2,4,6-trimethylbenzoyldiphenylphosphine oxide.

Preferably, multifunctional photoinitiators are utilized in the adhesive composition. The use of multifunctional photoinitiators further reduces the possibility of photoinitiator or fragments of the photoinitiator from migrating. Examples of suitable multifunctional photoinitiators include, but are not limited to, the Esacure KIP 100 (a mixture of 70% of an oligomeric α-hydroxy acetophenone and 30% of dimethyl hydroxy acetophenone), KIP 150, Esacure KTO-46 (blend of trimethylbenzophenone, polymeric hydroxy ketone, and trimethylbenzoyldiphenyl phosphine oxide), and Esacure ONE (difunctional alpha-hydroxyketone photoinitiator), all commercially available from Lamberti S.p.A., Gallarate, Italy).

The Applicant has found that when the adhesive composition of the present invention comprises the above mentioned multifunctional photoinitiators, it can be cured even employing a curing radiation having a low energy, i.e., having a wavelength ranging from 400 to 450 nm (violet light) and even ranging from 450 to 500 nm (blue light). This is particularly advantageous when curing components (like covers) of biological devices already filled with biological fluids that could be altered, or even destroyed, by exposure to radiation of high energy (like UV radiation having wavelength lower than 400 nm).

Suitable thermal initiators include organic peroxides in the form of diacyl peroxides, peroxydicarbonates, alkyl peresters, dialkyl peroxides, perketals, ketone peroxides and alkyl hydroperoxides, and also azo compounds. Concrete examples of such thermal initiators are dibenzoyl peroxide, tert-butyl perbenzoate, tert-butylperoxide, methylethylketone peroxide, and azobisisobutyronitrile.

The acrylic adhesive composition of the present invention preferably comprises from about 0.01% to about 2% by weight of a flow agent, based upon the total weight of the composition. In a preferred embodiment, the composition includes from about 0.02% to about 1% by weight of a flow agent. As used herein, "flow agent" means a suitable surface wetting or leveling agent. Preferably, the flow agent is a siloxane. More preferably, the siloxane is polyester modified dimethyl polysiloxane. A suitable commercially available product is Byk 310® (Byk Chemie; Wallingford, Conn.). Most preferably, the composition includes about 0.1% of Byk 310®.

The acrylic adhesive composition of the present invention preferably comprises from about 1% to about 20%, preferably from about 2% to about 15% by weight, based upon the total weight of the composition, of at least one coupling agent. The coupling agent can especially be a compound chosen from the silane compounds, such as, for example, aminosilanes, and unsaturated silanes such as a vinylsilane or a methacrylsilane.

Examples of suitable silane compounds include, but are not limited to, the commercially available vinyltri(β-methoxyethoxy)silane (A172) or γ-methacryloxypropyltrimethoxysilane (A174), both marketed by Union Carbide.

The Applicant has found that the addition of the above mentioned silane compounds can improve the adhesion between glass and other surfaces, like silicon and plastic materials, like polymethylmethacrylate (PMMA) and styrene acrylonitrile (SAN).

The acrylic adhesive composition of the present invention preferably comprises from about 1% to about 20%, preferably from about 5% to about 10% by weight, based upon the total weight of the composition, of at least one oxygen scavenger.

The oxygen scavenger can especially be a compound chosen from substituted phenols, such as, for example, butylated hydroxy toluene (BHT) and mono-t-butyl hydroquinone (MTBHQ) and aromatic amines, such as, for example, alkylated diphenyl amines and naphthylamines. BHT is commercially available from the Uniroyal Chemical Company, while MTBHQ is commercially available from the Eastman Chemical Company. Alkylated diphenyl amines are commercially available from Monsanto, under the Flectol tradename series. Naphthylamines are commercially available from Mobay, under the Vukanox tradename series.

When the adhesive composition of the present invention comprises an oxygen scavenger, the curing step can be also performed in the presence of oxygen. This is particularly advantageous when the biomedical device comprises areas or zones, like chambers isolated form a valve system, difficultly reached by a nitrogen flow.

The adhesive composition of the present invention can be advantageously employed for assembling the components of a biomedical device for the distribution or containment of biological substances. As described above, the components of the biomedical device to be joined can be made of different materials, such as inorganic materials, like, for example, silicon, glass, aluminum and other metals conventionally employed, or plastic materials, like, for example, polymethylmethacrylate (PMMA), cyclic olefin copolymers (COC), polycarbonates (PC), styrene acrylonitrile copolymers (SAN), and the like. The adhesive composition of the present invention has been proven to be able to join the components made of the same or different material.

Biomedical devices for the distribution or containment of biological substances are known in the art.

As indicated above, a feature of a biomedical device for the distribution of biological substances is the provision of a thermal or piezoelectric ejection head to deposit a quantity of the biological fluid onto a substrate surface. Thermal and piezoelectric ejection heads are well known in the art of conventional printing and document production.

As is known to those of skill in the art, thermal and piezoelectric ejection heads typically have at least the following components: (a) an orifice; (b) an ejection chamber; and (c) an actuating element, which can be a heating or piezoelectric element. Ejection heads are typically formed on a silicon substrate comprising the electronic components to operate the actuating element.

The size of the orifice is sufficient to produce a spot of suitable dimensions on the substrate surface, where the orifice generally has a diameter ranging from about 1 to 1000 µm, usually from about 5 to 100 µm and more usually from about 10 to 60 µm.

The ejection chamber has a volume ranging from about 1 pl to 10 nl, usually from about 10 pl to 5 nl and more usually from about 35 pl to 1.5 nl.

The actuating element is realized to deliver a quick energy pulse, either in the thermal or pressure form. The heating element is capable of achieving temperatures sufficient to vaporize a sufficient volume of the biological fluid in the ejection chamber to produce a drop of a predetermined volume of biological fluid from the orifice. Generally, the heating element is capable of attaining temperatures of at least about 100° C., usually at least about 400° C., and more usually at least about 700° C., where the temperature achievable by the heating element may be as high as 1000° C. or higher. The piezoelectric element is capable to change its dimension and to reduce the volume of the ejection chamber under the action of an electrical pulse to produce a pressure able to eject a drop of a predetermined volume of biological fluid from the orifice.

A barrier layer defining the microhydraulic of the biomedical device is usually laminated on the silicon substrate. Alternatively, the barrier layer may also be preformed and then assembled on the silicon substrate. The barrier layer is usually made with a photopolymer compound and define the supply chamber(s) and the microchannels supplying the biological fluid to the ejection chamber. Representative photopolymer compounds suitable for fabricating the barrier layer include but are not limited to: (1) epoxy polymers; (2) acrylic and melamine copolymers, (3) epoxy-acrylate copolymers, and (4) polyimides, although materials generally classified as photoresists or solder-masks can be used for this purpose. The barrier layer will have a thickness of from about 5 to about 50 µm, preferably from 10 to 40 µm although this value may be varied as needed. The microchannels have a diameter ranging from 100 to 300 µm, preferably from 150 to 250 µm.

At least one additional layer is then assembled on the barrier layer. The additional layer(s) define(s) supply channels having a size progressively increasing from the lowermost layer to the uppermost layer. The last additional layer is provided with supply openings for supplying the biological fluid connected to reservoir chambers for containing the biological fluid. In turn, the reservoir chambers are connected to the supply chamber(s) of the barrier layer through the above mentioned supply channels. The diameter of the supply channels starts from a 300 µm up to 1000 µm, and the diameter or diagonal (depending of its shape) of the reservoir chambers can be up to 2 mm. The additional layer(s) may be made of plastic material, such as, for example, polymethylmethacrylate (PMMA) or styrene acrylonitrile (SAN), glass, or a combination thereof.

Finally, a cover layer can be optionally assembled on the uppermost layer to seal the biomedical device after the biological fluid has been supplied to substantially fill the above mentioned reservoir chambers, supply channels and supply chambers.

In turn, a feature of a biomedical device for the containment of biological substances is the provision of a discrete microarray of capture probes immobilized at specific locations of a solid substrate to be used in biological assays, for instance to examine analyte biological fluids, such as human blood or tissue samples, for the presence and/or concentration of certain bacteria, viruses and/or fungi. Such biomedical device are commonly known as microarray biochip, or simply biochip. In particular, a biomedical device for the containment of biological substances can be constituted by (i) a transparent solid substrate on which a discrete microarray of capture probes has been deposited (ii) a containing chamber realized by photolithographic technique in a polymeric layer to confine biological samples (serum, blood, cells, oligomers and so on) and reagents in correspondence with such a microarray, (iii) a cover with input and output channels through which the biological samples are introduced and washed away.

The assembling of the several components of the above described biomedical devices is advantageously made by (i) forming a film of the adhesive composition of the present invention on at least one surface of the components to be joined, (ii) contacting the at least one surface of the components to be assembled, and (iii) curing the adhesive composition.

The film forming step (i) can be advantageously performed by spray coating techniques. The spraying coating apparatus typically requires to employ liquid having a viscosity lower than 100 cPoise. Liquids having a viscosity higher than 100 cPoise can also be used, but they require dedicated and expensive spraying coating apparatus, such as, for example, EFD (Engineered Fluid Dispensing) apparatus. The adhesive composition of the present invention advantageously has a viscosity lower than 100 cPoise, preferably lower than 80 cPoise. Accordingly, the adhesive composition of the present invention has a viscosity compatible with the requirements of spraying coating apparatus. This allows to avoid the use of organic solvents, which could potentially damage the plastic materials, and then allows to realize biomedical device with plastic materials.

Accordingly, the above mentioned film forming step (i) is advantageously performed in the substantial absence of any solvent, i.e., it is solvent-free. The use of the adhesive composition of the present invention allows to obtain a coated film having a constant and homogeneous thickness. The thickness of the coated film of adhesive composition is not particularly limited, and depends on the kind of apparatus employed to coat it and to the desired application. The thickness can range from about 1 µm (the lower limit being often dependent from the spraying apparatus specifications) to about 500 µm, and even more. However, the thickness of the coated film of adhesive composition preferably ranges from about 5 µm to about 100 µm.

The Applicant has found that the surface of the materials treated with the adhesive composition of the present invention which remain exposed, i.e., not joined to the surface of another material shows several improved characteristics.

First, the material surface has improved wettability, so allowing an easy diffusion of the biological fluids, typically having an aqueous base, into the biomedical device. The wettability is even more important in devices containing microhydraulic conduits wherein the flow of the fluids depends on capillarity forces and interactions between the fluid and the contacting surface. The wettability of the material surface covered with the adhesive composition of the present invention, when measured with the contact angle method by using a drop of water contacting the adhesive composition layer, is equal to or lower than 50°, preferably lower than 40°, and more preferably lower than 35°.

Second, the material surface has improved biocompatibility and exhibits excellent antifouling and protective properties. In other words, the surface of the materials treated with the adhesive composition of the present invention neither links external components contained in the biological fluids contacting it, nor releases internal components which could alter the composition of the biological fluids contacting it.

Preferably, the surface of the components to be joined is previously subjected to a plasma treatment. Plasma treatment is a widely known processing technology that aims at modifying the chemical and physical properties of a surface by using a plasma-based material. Plasma treatment includes plasma activation, plasma modification, plasma functionalization and plasma polymerization. Plasma processing is widely used in the field of electronics, automotive, textile, medical and aeronautic. A general review about plasma technology can be found on the Europlasma internet site at http://www.europlasma.be/pageview.aspx.

The plasma treatment is performed by flowing a plasma gas on the surface of the components in an apparatus comprising a plasma chamber powered with a couple of electrodes. Any conventional plasma gas can be used, provided that it is free from oxygen, either in atomic and molecular form. The Applicant has observed that the presence of oxygen reduces the adhesion strength because the oxygen adsorbed on the surface inhibits the curing of the adhesive composition. The plasma gas is preferably selected from the group consisting of saturated and unsaturated hydrocarbons, nitrogen-containing hydrocarbons, nitrogen, ammonia, hydrogen, and mixture thereof. Saturated hydrocarbons, such as, for example, methane and ethane, and forming gas, a mixture of nitrogen and hydrogen with a 10%, preferably 5%, maximum content of hydrogen, are preferably used in the process of the present invention. More preferably, the forming gas useful in the process of the present invention comprises a mixture of 95% of nitrogen and 5% of hydrogen. Preferably, the mixture of methane and forming gas has a methane to forming gas weight ratio of from 1:5 to 5:1, more preferably from 1:3 to 3:1 and most preferably from 1:2 to 2:1.

The plasma apparatus typically includes a chamber containing positive and ground electrodes attached to a radio frequency (RF) generator. The chamber comprises a support which is positioned between the positive and ground electrodes. The support is properly isolated from the chamber walls. The components to be treated are preferably put on the support between the positive and ground electrodes. Alternatively, the components can also be put in contact with the positive electrode or the ground electrode. In operation, a vacuum is created within the chamber until a pre-selected pressure in the range of from 1 to 30 milliTorr, preferably from 5 to 20 milliTorr is reached.

The gas is usually introduced into the chamber for a time of from 15 seconds to 3 minutes until to achieve the desired flow rate and partial pressures. The flow rate is preferably comprised from 1 to 300 sccm, more preferably form 10 to 200 sccm, and most preferably from 50 to 150 sccm (sccm=Standard Cubic Centimeters per Minute). The partial pressures is preferably comprised from 10 to 500 milliTorr, more preferably from 30 to 300 milliTorr, and most preferably from 50 to 250 milliTorr. Once the flow rate and pressure in the chamber are stabilized, a high voltage is applied in the radio frequency range of the apparatus between the ground and the positive electrodes and is maintained for the required time. The radio frequency power is preferably in the range of from 10 to 1000 Watt, more preferably from 30 to 700 Watt, and most preferably from 50 to 400 Watt. Preferably, the plasma treatment is conducted for a period of time in the range of from 10 seconds to 60 minutes, more preferably from 20 seconds to 30 minutes, and most preferably from 30 seconds to 10 minutes.

The plasma treatment can be conducted under constant conditions, i.e., without modifying the above described values of gas flow rate, gas mixture, pressure, and power, or under variable conditions.

Advantageously, the contacting step (ii) is performed by using apparatus provided with centering means able to line up the components to be joined. Preferably, the contacting step (ii) is followed by the removal of the air possibly trapped between two surfaces. The air removal is preferably performed by subjecting the contacted surface to a reduced pressure, such as, for example, 50 mmHg or even less. Further, the excess of adhesive can also been removed from channels and/or recesses of the components by subjecting the components to the action of vacuum apparatus.

Advantageously, when using adhesive compositions comprising a coupling agent like a silane compound, a thermal treatment of from 1 to 30 minutes, preferably from 2 to 15 minutes, at a temperature of from 50 to 200° C., preferably from 80° to 150° C., is made after the formation of the film of adhesive composition.

Generally, the curing step (iii) can be performed by exposure to radiation having a wavelength in the UV-blue range, namely from 200 to 500 nanometers. The energy of the UV-blue radiation is absorbed by a photoinitiator, which is capable of converting the light energy into free radicals. The presence of the free radicals initiates a chain reaction which converts reactive monomer compounds into oligomers and ultimately into polymers. Advantageously, when the curing step is performed in the presence of biological compounds easily damaged by high energy UV-radiation, the curing step is performed by exposure to radiation having a wavelength in the violet-blue range, namely from 400 to 500 nanometers.

Usually, the curing step is performed under an oxygen-free atmosphere, typically under a nitrogen atmosphere, to avoid the above mentioned inhibiting effect that oxygen has on the radical polymerization. Anyway, when the adhesive composition of the present invention comprises an oxygen scavenger, like for example, tertiary aromatic amines, the curing step can be also performed in the presence of oxygen. This is particularly advantageous when the biomedical device comprises areas or zones, like chambers isolated form a valve system, difficulty reached by a nitrogen flow.

The curing step (iii) can also be performed by thermal treatment. In this case a thermal initiator (thermoinitiator) is preferably added to the polymerization mixture. The polymerization temperature depends primarily on the decomposition temperature of the thermal initiator, but is preferably not higher than 135° C., and in particular, not higher than 110° C. A combination of photochemical curing with thermal curing can also be employed. In this case, thermal curing is preferably performed after photochemical curing.

The amount of biological fluid required to fill the biomedical device is typically small, generally not exceeding more than about 10 usually not exceeding more than about 5 µl and in many embodiments not exceeding more than about 2 µl. As such, the amount of biological fluid that is wasted during filling is minimal. As such, fluid loading is highly efficient. Therefore, the biomedical device of the present invention is particularly suited for use with rare and/or expensive biological fluid samples.

Biological fluid samples include solution or suspension of biological molecular compounds such as, but not limited to, nucleic acids and related compounds (e.g. DNAs, RNAs, oligonucleotides or analogs thereof, PCR products, genomic DNA, bacterial artificial chromosomes, plasmids and the like), proteins and related compounds (e.g. polypeptides, monoclonal antibodies, receptors, transcription factors, and the like), antigens, ligands, haptens, carbohydrates and related compounds (e.g. polysaccharides, oligosaccharides and the like), cellular organelles, intact cells, biopolymers and the like.

The filled and optionally sealed biomedical distribution device can be used to deposit an extremely small quantity of the biological fluid on a proper support, where the support may be a planar structure, e.g., a slide, a reagent container, e.g., a well in a multiwell plate (such as the bottom of a well), a channel or micro structure, an array, and so on.

The biomedical distribution device of the present invention can be used to deposit a pico liter quantity of fluid onto an array surface. By "pico liter quantity" is meant a volume of fluid that is at least about 0.1 pl, usually at least about 1 pl and more usually at least about 10 pl, where the volume may be as high as 250 pl or higher, but generally does not exceed about 100 nL and usually does not exceed about 1 µl.

In turn, biomedical containment device of the present invention can be used with extremely small quantity of the biological sample fluid (like blood, urine, intestinal fluids or saliva), with improved cleaning and sterile conditions, and ease of use. Typically, the biomedical containment device of the present invention can contain from 10 µl to 500 µl of biological sample fluid depending on the volume of the containing chamber, which in turn depends on the chamber shape and thickness.

The use of the adhesive composition of the present invention presented several advantages.

As mentioned above, the cured composition exhibits excellent antifouling and adhesion properties.

Additionally, the surface of the materials treated with the adhesive composition of the present invention which remains exposed, such as, for example, the surface of supply chamber(s), microchannels, supply channels, and reservoir chambers, resulted to be biocompatible with the biological fluids. In other words, the surface of the materials treated with the adhesive composition of the present invention neither links external components contained in the biological fluids contacting it, nor releases internal components which could alter the composition of the biological fluids contacting it.

Accordingly, the use of the acrylic adhesive composition of the present invention allows to avoid or limit all those surface treatments, like thermal treatment, corona treatment, plasma treatment, and so on, which conventionally are employed to improve the biocompatibility and antifouling properties.

Moreover, the possibility of curing the adhesive composition of the present invention by exposure to radiation of low energy (like violet-blue radiation having wavelength in the range of from 400 to 500 nm) allows to avoid the alteration, or even the destruction, of the biological substances like proteins, enzymes, antibodies and antigens contained in the biomedical device. This is particularly advantageous when curing the adhesive composition for assembling components (like covers) of biological devices already filled with biological fluids that could be altered, or even destroyed, by the exposure to radiation of high energy (like UV radiation having wavelength lower than 400 nm).

BRIEF DESCRIPTION OF THE DRAWINGS

Further features and advantages will become more apparent from the detailed description of a preferred, but not exclusive, embodiment of a biological device assembled with the adhesive composition of the present invention. This description will be set out hereinafter with reference to the accompanying drawings, given by way of non-limiting example, in which

FIG. 3 is a schematic cross sectional view of an embodiment of the microarray biochip of the present invention.

FIG. 4 is a schematic top view of an embodiment of the microarray biochip of the present invention.

DETAILED DESCRIPTION

The following will describe, with reference to the figures, a preferred embodiment of the invention.

Figure 1:
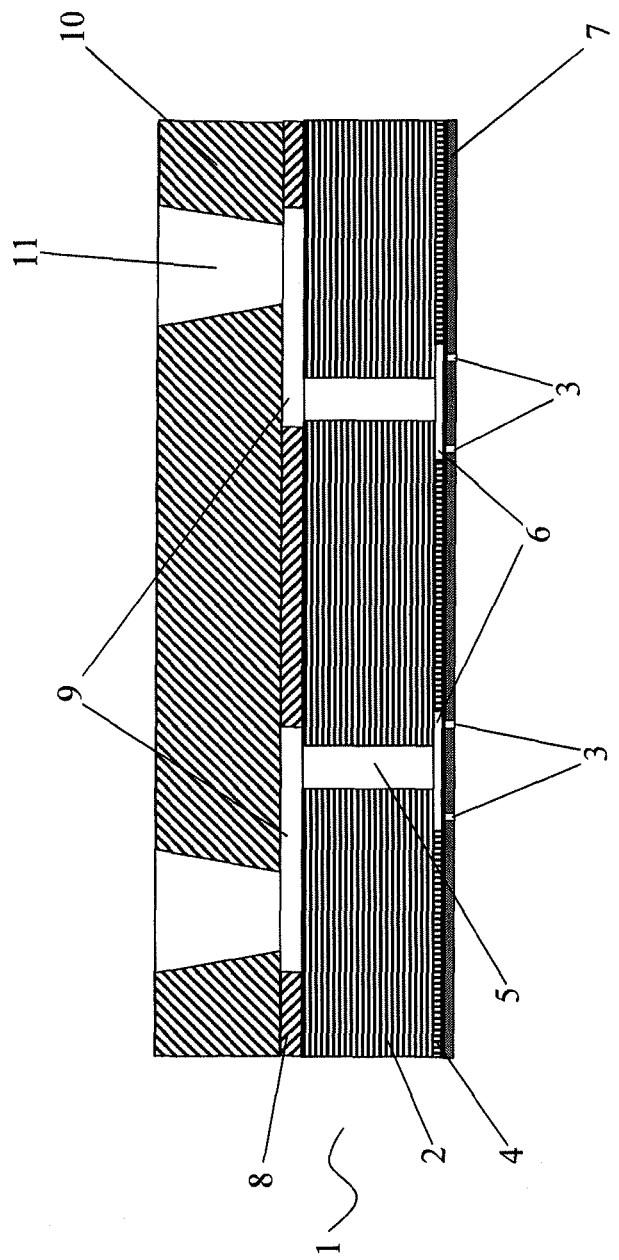
FIG. 1 is a schematic cross sectional view of an embodiment of the ejection head of the biological device of the present invention.

FIG. 1 shows the ejection head 1 of a biomedical device according to the present invention. The ejection head comprises a substrate 2, a barrier layer 4 and a nozzle layer or plate 7. The substrate 2 is generally made of silicon. The substrate 2 has supply channels 5 and, on the surface facing the barrier layer 4, several metallic layers (not shown) to make up the actuating element, typically a heating element or a piezoelectric element, and the active electronic components. The barrier layer 4 is made of photopolymer. The barrier layer comprises a set of ejection chambers 6 and the microhydraulic channels (not shown) realized by means of photolithographic techniques The nozzle layer or plate 7 comprises orifices 3 in the correspondence of the actuating element.

The substrate 2 on the surface opposite the barrier layer 4, supports a second barrier layer 8 made of photopolymer, wherein a set of channels 9 are realized by means of photolithographic techniques. The channels 9 are communicating with the supply channels 5 of the silicon substrate 2. Alternatively, as shown in FIG. 2, the second barrier layer 8 can be omitted and the channels 9 are directly realized by etching techniques within the silicon substrate 2.

A layer 10 provided with supply channels 11 is joined onto the second barrier layer 9, or alternatively onto the silicon substrate 2. In the latter case, the proper adhesion of the layer 10 to the silicon substrate 2 is obtained by means of the adhesive composition of the present invention. The layer 10 can be made of glass or plastic, like PMMA or SAN.

Figure 2:
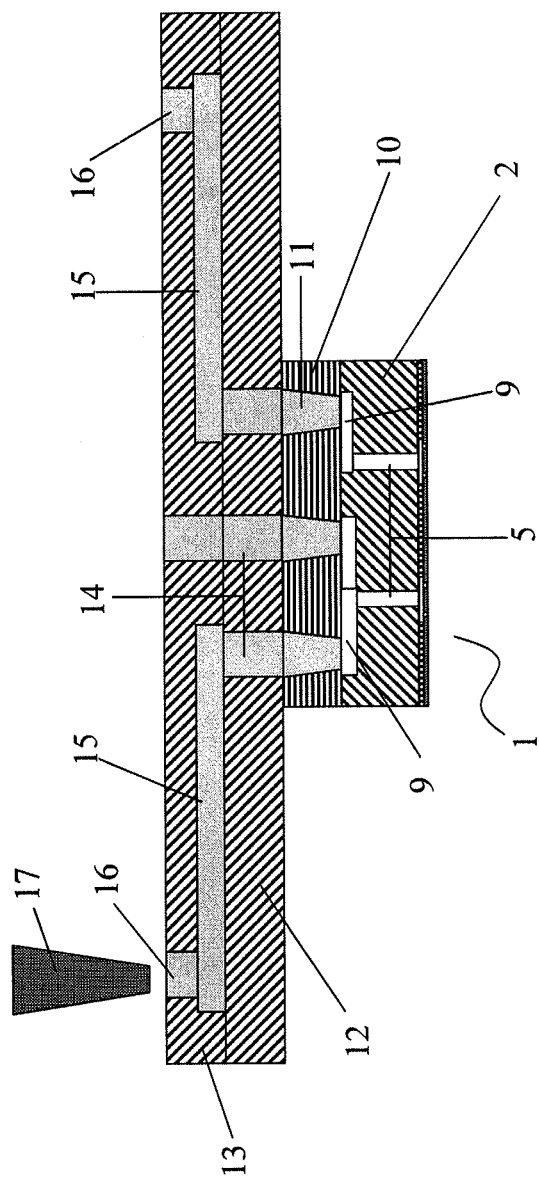
FIG. 2 is a schematic cross sectional view of an embodiment of the biological device of the present invention.

FIG. 2 shows the ejection head 1 of FIG. 1, further provided with two additional layers 12 and 13 having supply channels 14, reservoir chambers 15 and supply openings 16 for supplying the biological fluid from a pipette 17. The additional layers 12 and 13 can be made of glass or plastic, like PMMA or SAN. The proper adhesion of the lower and upper surface of layer 12 to layers 10 and 13, respectively, is obtained by means of the adhesive composition of the present invention. Moreover, the adhesive composition of the present invention is sprayed in such a way to form, after curing, a layer covering the whole surface of the channels and chambers realized into the plastic or glass layers 10, 12, 13, and the silicon substrate 2. As explained above, the cured adhesive composition layer provides to the walls of such channels and chambers the proper biocompatibility and wettability without the need of expensive and potentially damaging treatments.

FIGS. 3 and 4 show different views of an embodiment of a microarray biochip 20 according to the present invention. The microarray biochip 20 comprises a transparent substrate 21 on which a suitable pattern of several different biomolecules 22 has been deposited, and a chamber 23 to confine biological samples (serum, blood, cells, oligomers and so on) and reagents. The chamber is realized within a photo-patterned polymeric layer 24. A cover 25 closes the microarray biochip 20. The cover 25 is provided with input and output holes 26 to introduce and then wash away the biological samples and reagents. A thin layer of acrylic adhesive composition 27 is interposed between the photo-patterned polymeric layer 24 and transparent substrate 21 to join them together. The acrylic adhesive composition is applied, for example, by spraying method, to the assembly of the cover 25 and polymeric layer 24 after the photo-etching of the polymeric layer 24 to form the chamber 23. Accordingly, a thin layer of acrylic adhesive composition 28 is also deposited on the cover as well as on the walls of both the chamber 23 and the input and output holes 26. This allows to provide the proper wettability and biocompatibility to the walls contacting the biological samples and reagents, avoiding both the retaining of biological compounds and/or the release of contaminants.

The present invention will be further illustrated below by means of a number of preparation and evaluation examples of adhesive composition, which are given for purely indicative purposes and without any limitation of this invention.

EXAMPLES

A set of adhesive compositions according to the present invention has been prepared by using the ingredients and the amount of the following Table 1.

TABLE 1

|      | TMPEOTA | PETA | PEGMM | BYK310 | IMPP | EC 1 | EC 2 | A174 |
|------|---------|------|-------|--------|------|------|------|------|
| AB11 | — | 71 | 20.0 | — | 9 | — | — | — |
| AB12 | 74.1 | — | 21.9 | 0.03 | — | 4 | — | — |
| AB12.1 | 69.2 | — | 21.8 | 0.03 | — | 9 | — | — |
| AB15 | 71.1 | — | 21.8 | 0.03 | — | — | 7 | — |
| AB31 | 70.1 | — | 17.8 | 0.03 | — | — | 12 | — |
| AB34 | 70.0 | — | 14.0 | 0.03 | — | 4 | 12 | — |
| AB34.1 | 70.0 | — | 13.9 | 0.10 | — | 4 | 12 | — |
| AB35 | 68.9 | — | 10.0 | 0.10 | — | 4 | 12 | 5 |
| AB36 | 66.5 | — | 8.4 | 0.10 | — | 4 | 12 | 9 |
| AB37 | 75.7 | — | 11.0 | 0.10 | — | — | 7.7 | 5.5 |
| AB38 | 73.0 | — | 9.3 | 0.10 | — | — | 7.7 | 10 |
| AB39 | 55.0 | — | 21.9 | 0.10 | — | 4 | 12 | 7 |
| AB40 | 62.0 | — | 23.2 | 0.10 | — | — | 7.7 | 7 |

TMPEOTA: ethoxylated trimethylolpropane triacrylate, available from Aldrich
PETA: pentaerythritol triacrylate, available from Aldrich
PEGMM: polyethylene glycol monomethacrylate, available from Aldrich
BYK310: polyester modified dimethyl polysiloxane, available from Byk Chemie; Wallingford, Conn
HMPP: Hydroxymethylpropiophenone, available from Aldrich
EC 1: Esacure One 75, available from Lamberti
EC 2: Esacure KTO-46, available from Lamberti A174: γ-methacryloxypropyltrimethoxysilane, available from Union Carbide.

Adhesion Test

The above described adhesive compositions were tested for evaluating their adhesion strength on different materials.

Each adhesive composition was employed to adhere the sample materials identified in the following Table 2. The samples were prepared by spraying the surface to be joined with adhesive composition. After contacting the surfaces to be joined, the adhesive composition was cured by exposure to UV-blue radiation. When using formulation containing only the EC2 photoinitiator, absorbing in the blue-violet region of the visible spectrum the exposure was made by using a LED system emitting from 415 to 435 nm produced by CCS Europe NV, Belgium. When using formulation containing the EC1 photoinitiator, absorbing in the UV region, either alone or in combination with EC2, the exposure was made by using a D lamp emitting from 200 to 450 nm produced by Fusion UV Systems GmbH. The radiated energy was about 800 mJ/cm$^2$.

The evaluation was made by measuring the breaking load or by detaching the sample materials by knife and visually observing the kind of detachment.

Knife Test

This simple test requires the use of a utility knife to separate two substrates adhered with a cured layer of adhesive composition. The test is able to establish whether the adhesion is at a generally adequate level. Performance is based on both the degree of difficulty to detach the substrates and the observation of the kind of detachment. The knife is forced between the two adhered surfaces and then the knife is used to produce a force perpendicular to the adhered surfaces, until to reach a complete detachment or a rupture of the sample. The detached surfaces are then observed to the optical microscope to evaluate their appearance.

Breaking Load Test

This test was performed by measuring with an Instron instrument the load needed to detach a first square sample of 5 cm$^2$ adhered to a second sample of the same material. In correspondence of the centre of the first sample, the second sample had a hole through which the load force is applied to the first sample until to provoke the detachment or the rupture.

The measure of the load force was made by using an Instron instrument. The breaking load reported in Table 2 refers to the value obtained for detaching the sample of 5 cm$^2$.

TABLE 2

|  | PMMA/PMMA | PMMA/ GLASS | SAN/ GLASS | SILICON/ GLASS |
|---|---|---|---|---|
|  | Breaking load (Kg) | Knife detachment | | |
| AB11 | 11 | A | A | B | C |
| AB12 | 23 | B | A | B | C |
| AB12.1 | 17 | A | A | B | C |
| AB15 | 20 | A | A | B | C |
| AB31 | 13 | A | A | B | C |
| AB34 | 20 | B | A | B | C |
| AB34.1 | 20 | B | A | B | C |
| AB35 | 22 | B | B | B | C |
| AB36 | 24 | B | B | B | C |

TABLE 2-continued

|  | PMMA/PMMA | PMMA/ GLASS | SAN/ GLASS | SILICON/ GLASS |
|---|---|---|---|---|
|  | Breaking load (Kg) | Knife detachment | | |
| AB37 | 20 | A | B | B | C |
| AB38 | 20 | A | B | B | C |
| AB39 | 16 | A | A | B | C |
| AB40 | 12 | A | A | B | C |

A Detachment of the adhesive
B Delamination of the adhesive
C Delamination of the adhesive and glass rupture The observation of the detachment by visual inspection with the optical microscope revealed three kinds of detachment. Detachment A is not desired. The detachment of the adhesive from the substrate meant that the adhesive force was weak. On the contrary, detachment B, and even more, detachment C was desired. Detachments B and C meant that the adhesive force was strong, and in particular, that it was stronger than the cohesive forces of the same adhesive material Storage Test in Air at Low Temperature Another set of the same sample materials of Table 2 were stored for one week and three weeks at a temperature of about −10° C. After storage, samples were immersed in an aqueous solution of iophenoxic acid and rhodamine to check the presence of detachment areas. The results are summarized in Table 3.

TABLE 3

|  | PMMA/ PMMA | | PMMA/ GLASS | | SAN/ GLASS | | SILICON/ GLASS | |
|---|---|---|---|---|---|---|---|---|
|  | 1 W | 3 W | 1 W | 3 W | 1 W | 3 W | 1 W | 3 W |
| AB11 | NO | NO | YES | YES | NO | YES | NO | NO |
| AB12 | NO | NO | YES | YES | NO | YES | NO | NO |
| AB12.1 | NO | NO | YES | YES | NO | YES | NO | NO |
| AB15 | NO | NO | YES | YES | NO | YES | NO | NO |
| AB31 | NO | NO | YES | YES | NO | YES | NO | NO |
| AB34 | NO | NO | YES | YES | NO | YES | NO | NO |
| AB34.1 | NO | NO | YES | YES | NO | YES | NO | NO |
| AB35 | NO | NO | NO | NO | NO | NO | NO | NO |
| AB36 | NO | NO | NO | NO | NO | NO | NO | NO |
| AB37 | NO | NO | NO | NO | NO | NO | NO | NO |
| AB38 | NO | NO | NO | NO | NO | NO | NO | NO |
| AB39 | NO | NO | YES | YES | NO | YES | NO | NO |
| AB40 | NO | NO | YES | YES | NO | YES | NO | NO |

Storage Test in Water at Room Temperature

A set of different material samples were sprayed with the above described adhesive compositions and cured under the same conditions described above. The samples were immersed in water at room temperature and stored for one week and three weeks. After storage, the chemical resistance and the adhesion of the cured adhesive composition layer was evaluated by visual inspection with an optical microscope of detachment areas. The results are summarized in Table 4.

TABLE 4

|  | PMMA | | SAN | | GLASS | | SILICON | |
|---|---|---|---|---|---|---|---|---|
|  | 1 W | 3 W | 1 W | 3 W | 1 W | 3 W | 1 W | 3 W |
| AB11 | NO | NO | NO | NO | NO | NO | NO | NO |
| AB12 | NO | NO | NO | NO | YES | YES | YES | YES |
| AB12.1 | NO | NO | NO | NO | YES | YES | YES | YES |
| AB15 | NO | NO | NO | NO | YES | YES | YES | YES |
| AB31 | NO | NO | NO | NO | YES | YES | YES | YES |
| AB34 | NO | NO | NO | NO | YES | YES | YES | YES |
| AB34.1 | NO | NO | NO | NO | YES | YES | YES | YES |
| AB35 | NO | NO | NO | NO | NO | NO | NO | NO |
| AB36 | NO | NO | NO | NO | NO | NO | NO | NO |
| AB37 | NO | NO | NO | NO | NO | YES | NO | YES |
| AB38 | NO | NO | NO | NO | NO | YES | NO | YES |
| AB39 | NO | NO | NO | NO | YES | YES | YES | YES |
| AB40 | NO | NO | NO | NO | YES | YES | YES | YES |

The data shown above demonstrated that all tested adhesive compositions exhibited a good adhesion between glass and silicon and between SAN and glass.

The adhesive compositions AB12, AB34, AB34.1, AB35 and AB36 showed the best results of adhesion between two samples of PMMA.

The adhesive compositions AB34 and AB34.1 showed the best results of adhesion between glass and SAN.

The adhesive compositions AB35 and AB36 showed the best results of adhesion between glass and PMMA.

The adhesive compositions AB35 and AB36 showed good adhesion between all tested materials and also a good resistance under the storage conditions both at temperature below zero and under immersion in water. The adhesive compositions AB37 and AB38 have comparable good adhesion and good resistance under the storage conditions at temperature below zero, but the cured layer on glass and silicon showed detachment areas after three weeks of storage under water, probably due to the lower amount of photoinitiators.

Wettability/Viscosity Test

The following Table 5 summarizes the results of the measurement of the wettability and viscosity.

The wettability was evaluated by measuring the contact angle of a drop of water on a cured adhesive composition layer by using a OCA 40 Micro Automatic Contact Angle measuring apparatus (produced by DataPhysics Instruments GmbH, Germany).

The viscosity was measured by using a dynamic oscillatory mechanical rheometer (Viscotech, Rheologica Instruments AB, Sweden).

TABLE 5

|  | Contact angle (°) | Viscosity (cP) |
|---|---|---|
| AB11 | 50 | 170 |
| AB12 | 30 | 79 |
| AB12.1 | 30 | 81 |
| AB15 | 30 | 50 |
| AB31 | 30 | 53 |
| AB34 | 30 | 82 |
| AB34.1 | 30 | 81 |
| AB35 | 37 | 58 |
| AB36 | 38 | 55 |
| AB37 | 35 | 48 |
| AB38 | 38 | 42 |
| AB39 | 31 | 57 |
| AB40 | 30 | 45 |

The invention claimed is:

1. A biomedical device for the distribution or containment of biological substances, wherein the biomedical device comprises at least two components adhered together with an adhesive composition comprising at least one polyol tri(meth)acrylate monomer and at least one polyalkylene glycol mono (meth)acrylate monomer.

2. The biomedical device according to claim 1, wherein said polyol tri(meth)acrylate monomer is selected from the group consisting of ditrimethylolpropane triacrylate (DiTMPTTA), iris-(2-hydroxyethyl)-isocyanurate triacrylate (THEICTA), dipentaerythritol triacrylate (DiPETA), ethoxylated trimethylolpropane triacrylate (TMPEOTA), propoxylated trimethylolpropane triacrylate (TMPPOTA), ethoxylated pentaerythritol triacrylate (PETEOIA), propoxylated glyceryl triacrylate (GPTA), pentaerythritol triacrylate (PETA), trimethylolpropane triacrylate (TMPTA) and modified pentaerythritol triacrylate, triethyleneglycol trimethacrylate (TTEGTMA), tetraethyleneglycol trimethacrylate (TTEGTMA), polyethyleneglycol trimethacrylate (PEGTMA), trihydroxyhexane trimethacrylate (HTTMA), ethoxylated bisphenol A trimethacrylate, and trimethylolpropane trimethacrylate (TMPTMA).

3. The biomedical device according to claim 1, wherein said adhesive composition comprises from about 40% to about 90% by weight, based upon the total weight of said adhesive composition, of said at least one polyol tri(meth)acrylate monomer.

4. The biomedical device according to claim 1, wherein said polyalkylene glycol mono(meth)acrylate monomer is selected from the group consisting of polypropylene glycol monomethacrylate, polyethylene glycol monomethacrylate, polyethylene glycol-polypropylene glycol monomethacrylate, polypropylene glycol monoacrylate, polyethylene glycol monoacrylate, polypropylene glycol-polytrimethylene monoacrylate, polyethylene glycolpolytetramethylene glycol monomethacrylate, methoxypolyethylene glycol monomethacrylate, perfluorealkylethyl-polyoxyalkylene mono methacrylate, and combinations thereof.

5. The biomedical device according to claim 1, wherein said adhesive composition comprises from about 5% to about 35% by weight, based upon the total weight of said adhesive composition, of said at least one polyalkylene glycol mono (meth)acrylate monomer.

6. The biomedical device according to claim 1, wherein said adhesive composition comprises from about 1% to about 25% by weight based upon the total weight of the composition of at least one radical initiator selected from the group of initiators sensitive to UV and/or blue radiation (photoinitiator) and thermal initiators (thermoinitiator).

7. The biomedical device according to claim 6, wherein said photoinitiator is selected from the group consisting of 2,2'-(2,5-thiophenediyl)bis(5-tert-butybenzoxazole); 1-hydroxycyclohexyl phenyl ketone; 2,2-dimethoxy-2-phenylacetophenone; xanthone; fluorenone; anthraquinone; 3-methylacetophenone; 4-chlorobenzophenone; 4,4'-dimethoxybeniophenone; 4,4'-diaminobenzophenone; Michler's ketone; benzophenone; benzoin propyl ether; benzoin ethyl ether; benzyl dimethyl ketal, 1-(4-isopropylphenyl)-2hydroxy-2-methylpropane-1-one; 2-hydroxy-2-methyl-1phenylpropane-1one; methylbenzoyl formate thioxanthone; diethylthioxanthone; 2-isopropylthioxanthone; 2-chlorothioxanthone; 2-methyl-1-(4-(methylthio) phenyl)-2-morpholinopropane-1-one; and 2,4,6-trimethylbenzoyidiphenylphosphine oxide.

8. The biomedical device according to claim 6, wherein said thermoinitiator is selected from the group consisting of organic peroxides and azo compounds.

9. The biomedical device according to claim 1, wherein said adhesive composition comprises from about 0.01% to about 2% by weight of a siloxane flow agent, based upon the total weight of the composition.

10. The biomedical device according to claim 1, wherein said adhesive composition comprises from about 1% to about 20%, based upon the total weight of the composition, of at least one silane coupling agent.

11. The biomedical device according to claim 1, wherein said adhesive composition comprises from about 1% to about 20%, based upon the total weight of the composition, of at least one oxygen scavenger.

12. The biomedical device according to claim 11, wherein said oxygen scavenger is selected from the group consisting of substituted phenols and aromatic amines.

13. A biomedical device for the distribution or containment of biological substances comprising at least one surface thereof covered with a cured acrylic adhesive composition layer having a wettability equal to or lower than 50°.

14. The biomedical device according to claim 13 wherein said cured acrylic adhesive composition layer is made with an adhesive composition comprising at least one polyol tri (meth)acrylate monomer and at least one polyalkylene glycol mono(meth)acrylate monomer, and the biomedical device comprises at least two components adhered together with the adhesive composition.

15. The biomedical device according to claim 13, wherein said biomedical device comprises a thermal or piezoelectric ejection head comprising an orifice, an ejection chamber and an actuating element on a silicon substrate, at least one barrier layer, and at least one additional layer, which may be a cover layer.

16. The biomedical device according to claim 15, wherein said biomedical device further comprises reservoir chambers and supply openings.

17. The biomedical device according to claim 13, wherein said biomedical device comprises a transparent substrate a chamber realized within a photo-patterned polymeric layer to contain biological samples and reagents, and a cover provided with input and output holes to introduce and then wash away said biological samples and reagents.

* * * * *